(12) United States Patent
Kiely (10) Patent No.: US 11,660,055 B2
(45) Date of Patent: May 30, 2023

(54) SYSTEM AND METHOD FOR POSITIONING A PATIENT WITHIN AN X-RAY APPARATUS

(71) Applicant: DATA INTEGRITY ADVISORS, LLC, Washington, DC (US)

(72) Inventor: Janid Patricia Blanco Kiely, Washington, DC (US)

(73) Assignee: DATA INTEGRITY ADVISORS, LLC, Washington, DC (US)

( * ) Notice: Subject to any disclaimer, the term of this patent is extended or adjusted under 35 U.S.C. 154(b) by 204 days.

(21) Appl. No.: 17/313,376

(22) Filed: May 6, 2021

(65) Prior Publication Data

US 2021/0298695 A1    Sep. 30, 2021

Related U.S. Application Data (63) Continuation of application No. PCT/US2021/023516, filed on Mar. 22, 2021.
(Continued)

(51) Int. Cl.
*A61B 6/04*     (2006.01)
*A61B 6/00*     (2006.01)

(52) U.S. Cl.
CPC .............. *A61B 6/04* (2013.01); *A61B 6/50* (2013.01); *A61B 6/5217* (2013.01)

(58) Field of Classification Search
CPC ............ A61B 6/04–0492; A61B 5/389; A61B 6/5217; A61B 5/0816; A61B 5/704; A61G 5/02
See application file for complete search history.

(56) References Cited

U.S. PATENT DOCUMENTS

2013/0345543 A1* 12/2013 Steibel, Jr ............. A61M 21/02
                                                                                    600/407
2014/0107390 A1    4/2014 Brown et al.
(Continued)

FOREIGN PATENT DOCUMENTS

WO    WO2014/028288 A1    2/2014
WO    WO2019/23 6317 A1   12/2019

OTHER PUBLICATIONS

Data Integrity Advisors, LLC, International Search Report and Written Opinion, PCTUS2021023516, dated Jul. 6, 2021, 9 pgs.

*Primary Examiner* — Boniface Ngathi N
*Assistant Examiner* — Milton Truong
(74) *Attorney, Agent, or Firm* — Morgan, Lewis & Bockius LLP (57) ABSTRACT

Systems and methods for positioning a patient during radiological measurements are provided. A biofeedback signal from the patient is received. While receiving the biofeedback signal from the patient and while the patient is positioned at a first position by the fixture, determining whether the biofeedback signal from the patient is indicative of the patient breathing at rest. Further, in accordance with a determination that the biofeedback signal from the patient is not indicative of the patient breathing at rest, articulating the patient using the fixture from the first position to a second position. In accordance with a determination that the biofeedback signal from the patient at the second position is indicative of the patient breathing at rest, obtaining radiological measurements of the patient with the patient positioned at the second position.

18 Claims, 9 Drawing Sheets

Related U.S. Application Data

(60) Provisional application No. 62/994,673, filed on Mar. 25, 2020.

(56) References Cited

U.S. PATENT DOCUMENTS

| | | |
|---|---|---|
| 2019/0083004 A1 | 3/2019 | Meir et al. |
| 2020/0008703 A1* | 1/2020 | Zeller .................. A61B 5/7285 |
| 2020/0164175 A1* | 5/2020 | Kim ..................... A61B 5/6891 |
| 2021/0121139 A1* | 4/2021 | Andreyev .............. A61B 6/541 |

* cited by examiner

Computer System 406

SYSTEM AND METHOD FOR POSITIONING A PATIENT WITHIN AN X-RAY APPARATUS

PRIORITY APPLICATIONS

This application is a continuation of International Application PCT/US21/23516, filed Mar. 22, 2021, which claims priority to U.S. Patent Application Ser. No. 62/994,673, filed Mar. 25, 2020, entitled "System and Method for Positioning a Patient within an X-Ray Apparatus," each of which is hereby incorporated by reference in its entirety.

TECHNICAL FIELD

The present disclosure relates to medical imaging and, more particularly, to systems and methods for positioning a patient within a medical imaging (e.g., x-ray) apparatus.

BACKGROUND

Computational modeling of human anatomy facilitates an understanding of the anatomical behavior that typifies different physiological conditions. While state-of-the-art imaging techniques can allow a physician to visualize anatomic behavior, the state-of-the-art technology that accurately images complex movements of the heart and lung is often too expensive to be widely adopted. Moreover, cardiac motion, e.g., deformation of the heart, which is an intricate process and unrelated to the breathing cycle may appear as noise in computed tomography (CT)-based or radiographic breathing motion measurements. Consequently, the accuracy of mathematical models that describe breathing motion will also be degraded by seemingly random heart motion. One way of addressing this issue is to remove lung motion from images by making patients hold their breath. While this approach stops the patient's breathing motion, crucial information on lung health (e.g., including lung capacity) may be hard to identify in these breath-hold images.

SUMMARY

The embodiments described herein provide a patient positioning fixture (PPF) for positioning a patient within an x-ray apparatus. The PPF includes a rotating platform on which the patient is positioned. The PPF is coupled with a computer system that includes one or more processors and memory. As described in PCT/US2019/064846, which is incorporated by reference in its entirety, the rotating platform rotates the patient with respect to an x-ray tube and detector panel (e.g., so that x-ray images of the patient may be obtained from different projection angles). For example, instead of rotating the x-ray tube and detector panel, the PPF rotates the patient between projection angles, acquires x-ray images at those projection angles, and keeps the patient's position substantially identical (e.g., fixed relative to the PPF) between rotations. In some embodiments, the x-ray images acquired at the different projection angles are used to reconstruct and model dynamics of the patient's lung (e.g., how the lung moves during the breathing cycle). In particular, a three-dimensional (3D) model of the patient's lung may be generated from two-dimensional (2D) images using the radon transformation. Substantially identical patient position across projection angles is an important aspect of this reconstruction: the object being reconstructed by its projections (e.g., the patient's lung) must be stationary (aside from movement from breathing) across all projection angles. In some embodiments, the problem of breathing motion is solved by measuring the patient's breathing phase and sorting images accordingly, so that different reconstructions are performed for different breathing phases.

Moreover, in some embodiments, the PPF places the patient in an optimal or near optimal position for capturing x-ray images at different projection angles. To do so, two criteria should be met: (1) the patient should have an open posture so that the patient's arms do not interfere with any of the x-ray projections, and (2) the patient should be able to breathe normally in the position. The latter is especially important when reconstructing biomechanical models of the patient's breathing (e.g., models of elastic modulus, etc., as described in PCT/US2019/064846). In some embodiments, this problem is solved by articulating the patient (e.g., rotating one body part of the patient relative to another via a mechanical joint of the PPF) while measuring a biofeedback signal of the patient. The biofeedback signal indicates whether the patients breathing is at rest. In some embodiments, if the computer system determines, using the biofeedback signal, that the patient is not breathing at rest, the computer system returns the patient to the last position at which the patient was breathing at rest.

To that end, the present disclosure provides a method of positioning a patient for the purpose of radiological measurements. The method is performed at a computer system with one or more processors and memory. The computer system is communicatively coupled with a fixture for positioning a patient during radiological measurements. The method comprises receiving a biofeedback signal from the patient. The method further includes, while receiving the biofeedback signal from the patient, determining, while the patient is positioned at a first position by the fixture, whether the biofeedback signal from the patient is indicative of the patient breathing at rest. The method further includes, in accordance with a determination that the biofeedback signal from the patient is not indicative of the patient breathing at rest, articulating the patient (e.g., moving or repositioning, via rotation of one or more joints of the patient) using the fixture from the first position to a second position. The method further includes, in accordance with a determination that the biofeedback signal from the patient, at the second position, is indicative of the patient breathing at rest, obtaining radiological measurements of the patient with the patient positioned at the second position.

Some implementations of the present disclosure provide a computer system (e.g., a server system or a local computer system), comprising one or more processors and memory storing one or more programs. The one or more programs store instructions that, when executed by the one or more processors, cause the computer system to perform any of the methods described herein.

Some implementations of the present disclosure provide a computer program product (e.g., a non-transitory computer readable storage medium storing instructions) that, when executed by a computer system having one or more processors, cause the computer system to perform any of the methods described herein.

Additional aspects and advantages of the present disclosure will become readily apparent to those skilled in this art from the following detailed description, where only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

The implementations disclosed herein are illustrated by way of example, and not by way of limitation, in the figures of the accompanying drawings. Like reference numerals refer to corresponding parts throughout the several views of the drawings.

DETAILED DESCRIPTION

Reference will now be made in detail to embodiments of the present disclosure, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

The implementations described herein provide various technical solutions for positioning a patient during radiological procedures.

Several aspects are described below with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

As used herein, unless specified or limited otherwise, relative terms such as "central", "longitudinal", "lateral", "front", "rear", "right", "left", "inner", "outer", "lower", "upper", "horizontal", "vertical", "above", "below", "up", "top", "bottom" as well as derivative thereof (e.g., "horizontally", "downwardly", "upwardly", etc.) should be construed to refer to the orientation as then described or as shown in the drawings under discussion. These relative terms are for convenience of description and do not require that the present disclosure be constructed or operated in a particular orientation.

As used herein, unless specified or limited otherwise, the terms "mounted," "connected," "coupled," "fixed" and the like are used broadly, and may be, for example, fixed connections, detachable connections, or integral connections; may also be mechanical or electrical connections; may also be direct connections or indirect connections via intervening structures; may also be inner communications of two elements, which can be understood by those skilled in the art according to specific situations.

As used herein, unless specified or limited otherwise, a structure in which a first feature is "on" or "below" a second feature may include an embodiment in which the first feature is in direct contact with the second feature, and may also include an embodiment in which the first feature and the second feature are not in direct contact with each other, but are contacted via an additional feature formed between the first and second features. Furthermore, a first feature "on," "above," or "on top of" a second feature may include an embodiment in which the first feature is right or obliquely "on," "above," or "on top of" the second feature, or just means that the first feature is at a height higher than that of the second feature; while a first feature "below," "under," or "on bottom of" a second feature may include an embodiment in which the first feature is right or obliquely "below," "under," or "on bottom of" the second feature, or just means that the first feature is at a height lower than that of the second feature.

As used herein, the verb "articulate" means to move (e.g., rotate) via a joint. For example, articulating a patient from a first position to a second position means to move (e.g., rotate) one part of the patient's body with respect to another part of the patient's body (e.g., via a jointed portion of a patient positioning fixture). Articulation of the patient is distinct from rotation of the entire patient from a first orientation with respect to an x-ray apparatus to a second orientation with respect to the x-ray apparatus. For example, in some embodiments, the patient is first articulated to a position at which to acquire x-ray images from multiple orientations, the position is fixed, and the patient is rotated in the fixed position between the multiple orientations.

As used herein, unless specified or limited otherwise, the terms "biofeedback sensors," "sensors," and other variations are intended to include acoustic sensors, accelerometers (e.g. surface mechanomyoreceptors), optical, and impedance sensors or measurements. For simplicity, "electromyographic" sensors are used, in some embodiments, as an example of biofeedback sensors throughout document.

As used herein, unless specified or limited otherwise, the terms "phases," "breathing phases," "lung phases," and other such variations are intended to include the inhalation (e.g., where there is a net movement of air into a patient's lungs) and exhalation (e.g., where there is a net movement of air out of a patient's lungs) portions of a patient's breathing process. For example, a first breathing phase refers to a portion of time with a first pressure, a first lung volume, and a first airflow change. In some embodiments, the inhalation portion of a patient's breathing is further divided into late inhalation, mid-inhalation, and early inhalation phases. In some embodiments, the exhalation portion of a patient's breathing is further divided into late expiration, mid-expiration, and early expiration breathing phases. In some embodiments, a breathing process further includes a resting phase (e.g., an intermediary phase between inhalation and exhalation) where there is no net movement of air. Breathing is a mechanical process, which in many types of breathing includes movement of the patient's diaphragm. Inhalation typically, for healthy patients, includes active contraction of muscles in order to increase lung capacity and bring in air. Likewise, the exhalation of healthy patients typically includes passive contraction of muscles to expel air from the lungs.

Figure 1A:
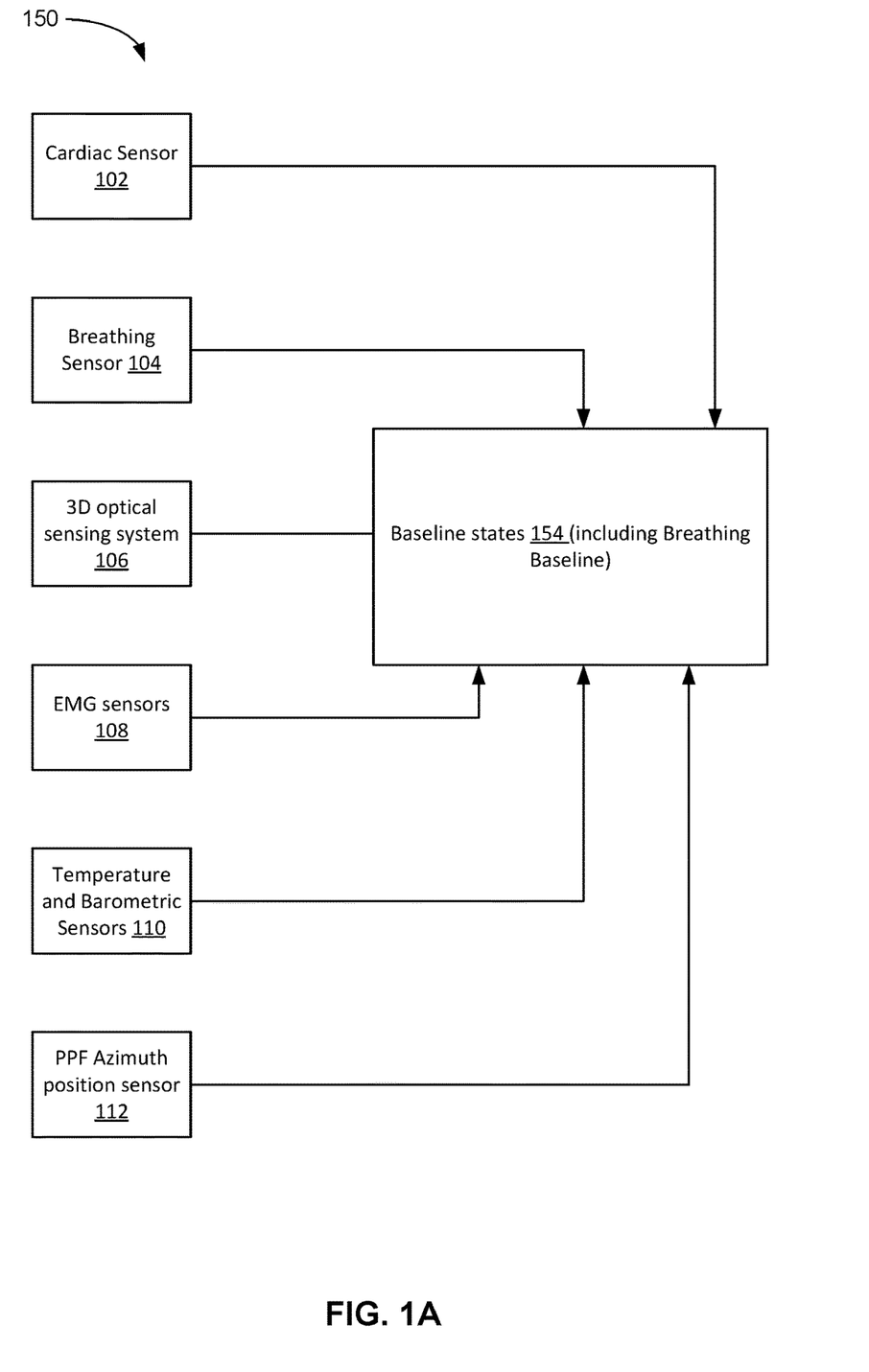
FIGS. 1A-1C illustrate a process for positioning a patient for medical imaging (or another radiological process) using a patient positioning fixture (PPF).
Figure 1B:
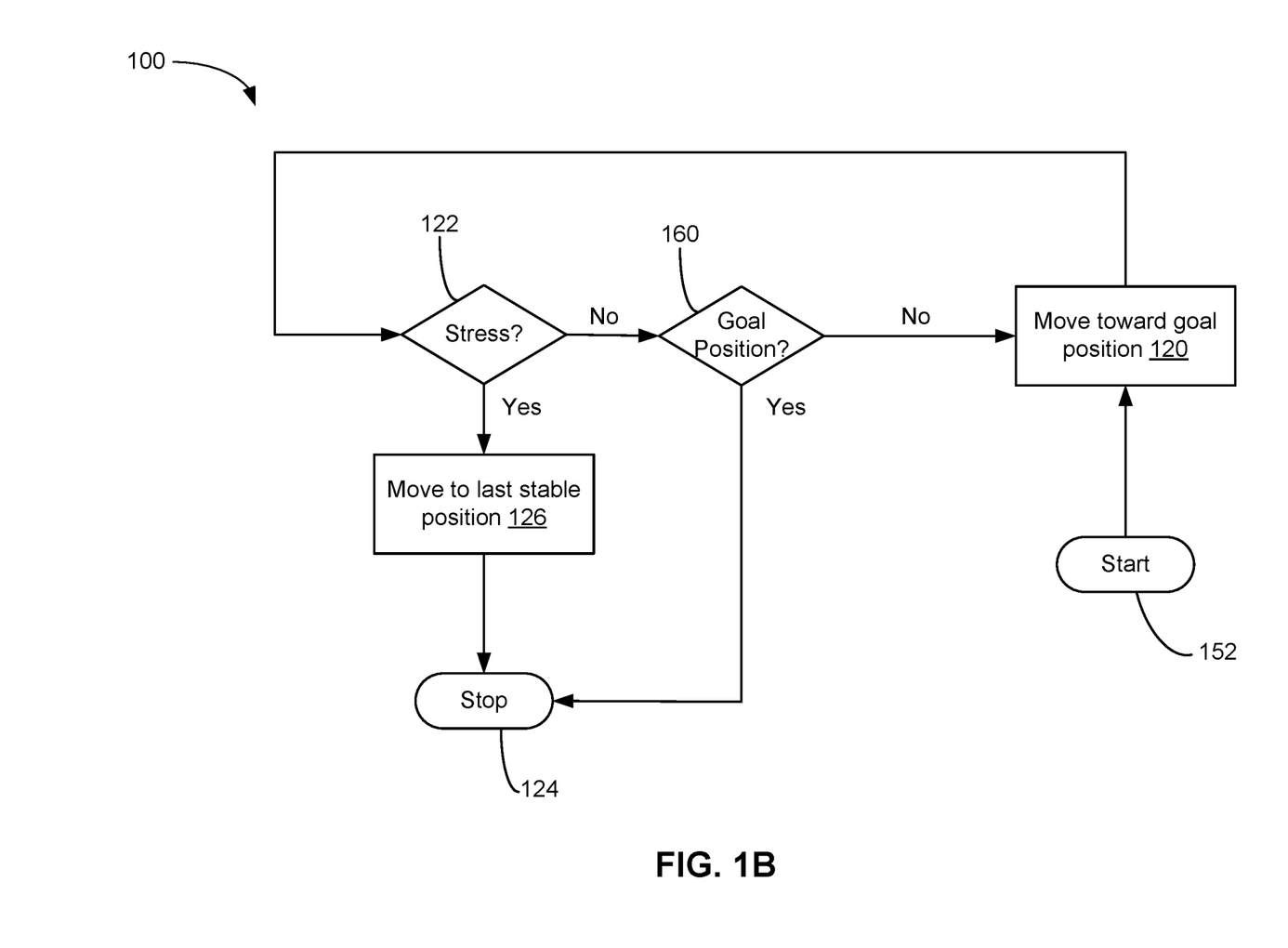
Figure 1C:
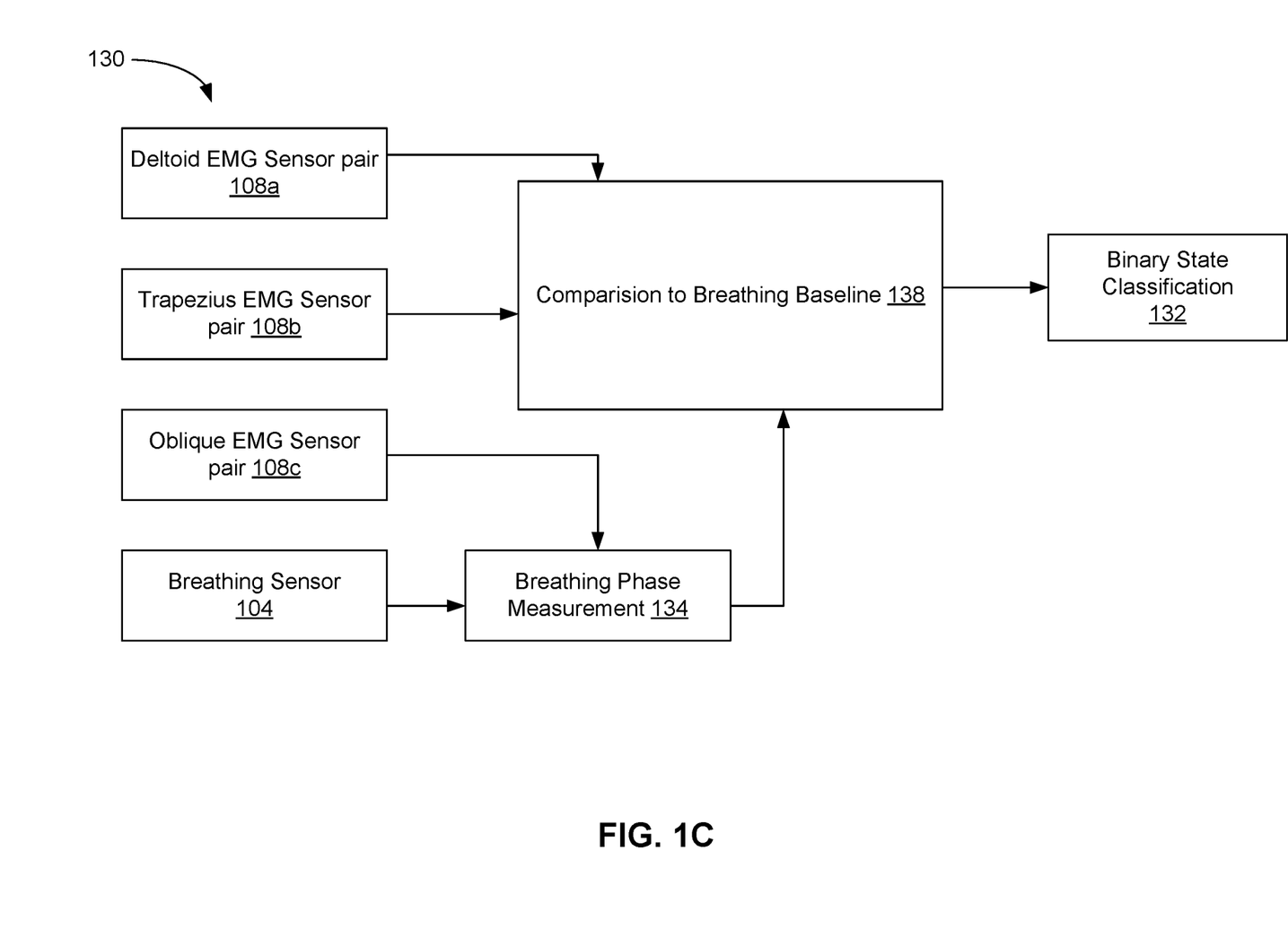

FIGS. 1A-1C illustrate a process for positioning a patient for medical imaging (or another radiological process) using a patient positioning fixture (PPF). In some embodiments, the purpose of the PPF is to position a patient to enable x-ray imaging of the patient (e.g., for diagnostic purposes). The embodiments described herein provide methods and devices that adjust the fixed position of the patient within the PPF prior to acquiring the x-ray images at the respective projection angles. The goal of the adjustment is two-fold: the patient should be positioned so that x-ray images can be obtained at a wide range of projection angles (e.g., without the patient's arm angle interfering with the projections) and the position of the patient should not change the patient's breathing (e.g., pinning the patient's arms behind his or her back would alter the patient's breathing). To that end, the methods and devices described herein move the patient toward an optimal position (e.g., goal position 160) while measuring signals indicative of the patient's breathing.

Training the PPF to Determine Optimum Positioning.

FIG. 1A illustrates a training process 150. To that end, in some embodiments, training process 150 serves to identify baseline states 154 for a patient. In some embodiments, baseline states 154 are determined individually for each patient. In some embodiments, baseline states 154 are determined (e.g., standardized) for particular classes of patients (e.g., classes such as age, health condition, etc.). In various embodiments, the baseline states 154 include one or more of the following characteristics (e.g., states) of the patient (note that not all of these states are necessarily used in adjusting the positioning of the patient)

Via a cardiac sensor 102 (e.g., electrocardiogram (ECG) sensor)—baseline states 154 optionally include the patient's unique cardiac rhythm, ECG mark events, and patient's unique statistical timing norms for the heartbeat mark events. From this information, the quiescent phase cardiac trigger pulse timing and gate window is computed and off-nominal mark event timing deviations established.

Via a breathing sensor 104—baseline states 154 optionally include the patient's lung volume and breathing curve histogram, and statistical timing norms for the breathing curve. In some embodiments, breathing sensor 104 is used to determine a breathing phase. To that end, in some embodiments, the system computes the volumetric sample ranges for each unique breathing curve sample point, and determines the trigger window timing for each breathing phase sample. In some embodiments, the 3D imaging sensing system 106 (described below) is used as the breathing sensor. In some embodiments, the breathing sensor is a spirometer. During the imaging phase (after training), the breathing sensor is used to output a trigger pulse when the correct breathing phase is detected (via a time-series prediction algorithm).

Via a 3D optical sensing system 106—baseline states 154 optionally include the patient's physical position within the imaging frame of reference. In some embodiments, a 3D imaging system generates a 3D point cloud representing the patient's lungs. During the training period, internal tissue densities are estimated using models of attenuation factors for different types of tissue (e.g., bony and soft tissue). These models extrapolate internal bony anatomy (i.e., rigging) from visible bony anatomy (e.g., clavicle, ribcage, etc.). In some embodiments, the system determines the position boundaries that if exceeded would require correction to the patient position. During the imaging process (after the learning phase), if the system detects movement toward or exceeding the acceptable limits within the imaging frame, the system will use a haptic system (on each arm rest) to notify the patient to move toward the correct position. In some embodiments, the 3D optical sensing system comprises a LIDAR system, or any other 3D optical sensing system known in the field.

Via EMG sensors 108—baseline states 154 optionally include one or more breathing baselines. In some embodiments, electromyographic sensor pairs are attached (directly or indirectly) to the deltoid muscles and the trapezius muscles of a patient (and optionally the oblique muscles). In some embodiments, the sensor pairs provide feedback about the patient's breathing in real-time. These electromyographic sensor pairs produce signal patterns that are associated with classified respiratory (e.g., breathing/lung) phases (e.g., phases including late inhalation (LI), mid-inhalation (MI), early inhalation (EI), late expiration (LE), mid-expiration (ME), and early expiration (EE)). These associated electromyographic signal patterns form a breathing baseline for the patient. In some embodiments, each respiratory phase has a corresponding associated electromyographic breathing baseline. In some embodiments, the breathing baseline is determined for an entire set of respiratory phases. Subsequent to determining a breathing baseline of the patient, EMG signals for the deltoid and trapezius muscles are used, as described with reference to FIG. 1C, to determine whether the patient's breathing is at rest or not at rest (e.g., whether the EMG signal diverges from the baseline state).

Via temperature and barometric sensors 110—baseline states 154 optionally include the temperature and barometric pressure at the time each imaging cycle is started for accurate patient lung air mass volume and mass air flow computation.

Via a PPF azimuth position sensor 112—baseline states 154 optionally include a patient azimuth (e.g., an axis of the patient's torso). In some embodiments, the system determines an azimuth position of the patient/PPF at the beginning of the imaging process, and after the PPF changes patient azimuth before each position X-ray image set is taken. This information is required for each imaging angle to accurately compute and align the "3D image cubes" as described in PCT/US19/33751, filed May 23, 2019, which is hereby incorporated by reference in its entirety.

Positioning a Patient on the PPF so that the Patient is Breathing at Rest (e.g., is Breathing in a Baseline State).

With reference to FIG. 1B, after the training process 150, the automated positioning process 100 ensues. Using biofeedback signals from the patient (e.g., as described with reference to FIG. 1C), a starting position 152 of the PPF (e.g., of the patient in the PPF) is iteratively modified (e.g. by articulating the patient) to approach a goal position 160 of the PPF. The goal position 160 is one that maximizes available projection angles while simultaneously not imparting additional stress on the chest (e.g., opens the patient's chest up to the widest cone of angles for x-ray measurements while not affecting the patients breathing).

In some embodiments, iteratively modifying the position of the patient includes moving (120) the patient toward the goal position 160. The automated positioning process 100 includes determining (122) whether the patient's breathing is stressed at a current position. To that end, in some embodiments, the PPF mechanically articulates the patient (e.g., by moving components described with regards to FIGS. 2A-2C as shown in FIGS. 3A-3B). In some embodiments, mechanical articulation of a patient by the PPF comprises movement of a first component of the PPF (e.g., armrest 202, FIGS. 2A-2C) and movement of a second component of the PPF (e.g., armrest 204, FIGS. 2A-2C). In some embodiments, the first and second components are moved concurrently. In some embodiments, the first and second components are moved sequentially. While the PPF is mechanically articulating the patient, a binary state classification 132 (FIG. 1C) corresponding to positional chest stress of the patient is monitored. In some embodiments, the binary state classification 132 of the patient is monitored by the PPF. In some embodiments, the binary state classification 132 of the patient is monitored by an additional device (e.g., a smart watch, a heart rate monitor, etc.).

In accordance with a determination that the patient's breathing is stressed at the current position (e.g., when the binary state classification 132 indicates that additional stress is being applied to the patient's chest from the PPF position), the PPF articulation stops 124. In some embodiments, in accordance with a determination that the patient's breathing is stressed at the current position, the PPF returns the patient's position to the last recorded stable position 126. This process is repeated, in some embodiments, one or more times. Alternatively, this process is performed continuously (with the stress in block 122 being monitored continuously as the patient is moved). Thus, the PPF mechanically articulates the patient's shoulders, elbows, knees, etc. to the furthest extent possible toward the goal position 160 (e.g., to the point prior to where the articulation would cause additional musculature tension to the patient's mechanical respiratory function).

FIG. 1C illustrates a process 130 for determining whether the patient's breathing is stressed (in a process for making the determination in block 122, FIG. 1B), in accordance with some embodiments. In some embodiments, the output of process 130 is a binary state classification 132 (e.g., in which an outputted value of "1" represents at rest breathing, corresponding to a "no" at block 122, and an outputted value of "0" represents stressed breathing, corresponding to a "yes" at block 122). In some embodiments, EMG signals from one or more of deltoid EMG sensor pair 108a and trapezius EMG sensor pair 108b are compared (138) against the breathing baseline (as described with reference to FIG. 1A) to determine the binary state classification 132. In some embodiments, the breathing baseline is defined as a stable position for the patient where the patient's respiration is mechanically quiet (e.g., the tension across the patient's chest does not measurably alter the mechanics of lung tissue during respiration). Signal feature thresholds (e.g., threshold values for features of the breathing baseline) are calculated to determine deviance from features of the breathing baseline. In some embodiments, these features are extracted by a zero instruction set computer (ZISC). In some embodiments, another version of a reduced instruction set computer (RISC) architecture is used. In some embodiments, during the training phase the ZISC extracts the features of the breathing baseline. In some embodiments, the breathing baseline represents the deltoid muscle and trapezius muscle. In some embodiments, there are a total of six patterns representing the six breathing phases per sensor. In real-time function, the ZISC rapidly processes signal features so that regardless of breathing phase, a binary state classification 132 corresponding to stressed (not at rest breathing) and stable (at rest breathing) is generated.

In some embodiments, exterior oblique EMG sensor pair 108c measuring the external oblique muscles are used as an indication of (e.g., proxy for) diaphragm activation during respiration. The breathing phase measurement 134 (e.g., the respiratory signal) is associated (through concurrent, real-time measurement) with a specific electromyographic external oblique muscle signal pattern. When the diaphragm activates during respiration, an electrical signal will be measured across the external oblique muscle. The electromyographic signal's pattern changes during respiration so associating the measured electromyographic signal with the physiologic respiratory measurement (e.g., a volumetric measurement) leads to respiratory phase classification based on electromyographic measurement of the external oblique muscle. In this manner, a respiratory phase is determined based on the electromyographic signal. In some embodiment, a breathing sensor 104 is used to classify the breathing phase. As described in greater detail in PCT/US2019/064846, possible respiratory phases include late inhalation (LI), mid-inhalation (MI), early inhalation (EI), late expiration (LE), mid-expiration (ME), and early expiration (EE). In some embodiments, the correspondence between EMG signals and respiratory phase is determined uniquely for an individual patient.

In some embodiments, breathing phase measurement 134 of the patient is measured by the 3D optical sensing system (e.g., using tidal volume that is obtained via the ideal gas law). That is, in some embodiments, the 3D optical sensing system 106 is used to identify one or more breathing phases (e.g., the lung phases).

Figure 2A:
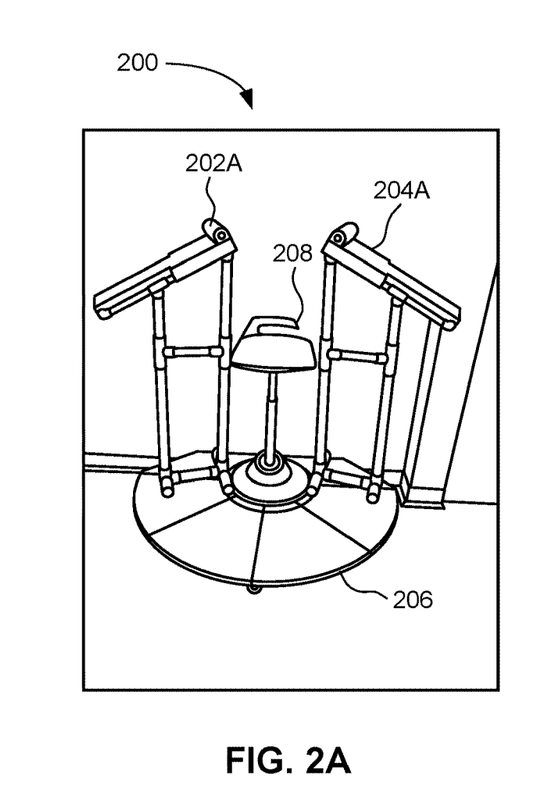
FIGS. 2A-2C illustrate a PPF (e.g., a rotatable, modular chair) for supporting a patient in multiple possible orientations, in accordance with some embodiments of the present disclosure.
Figure 2B:
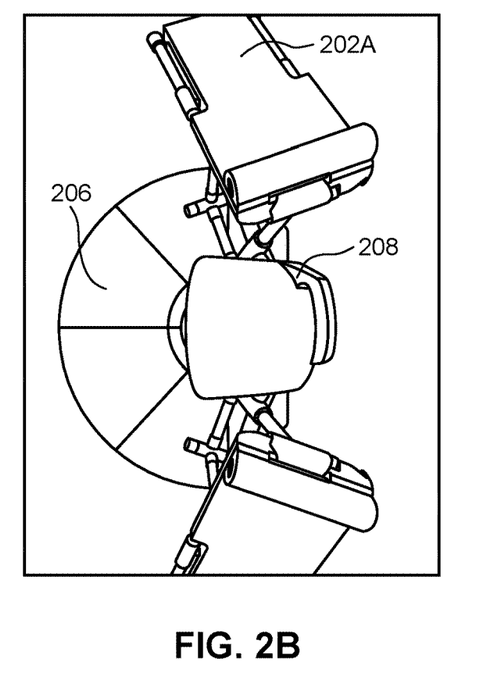
Figure 2C:
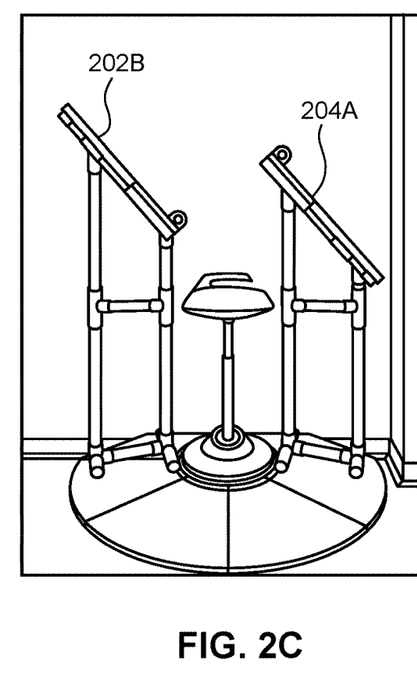
Figure 3A:
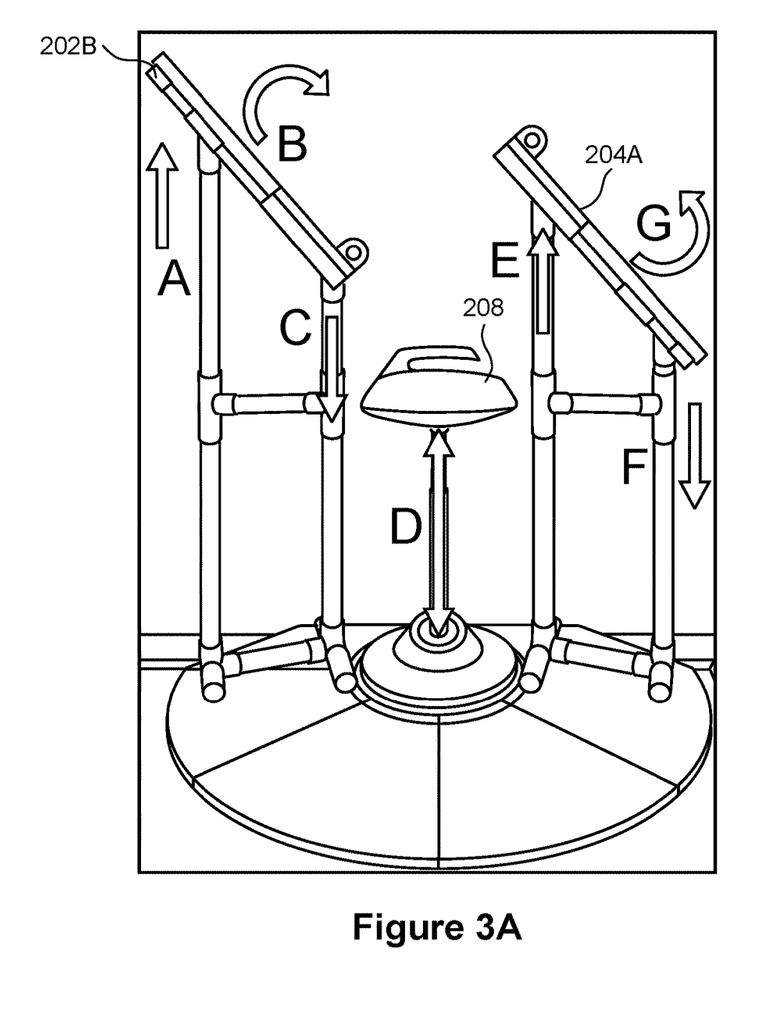
FIGS. 3A-3B illustrate a PPF including indications of exemplary movements of components of the PPF, in accordance with some embodiments of the present disclosure.
Figure 3B:
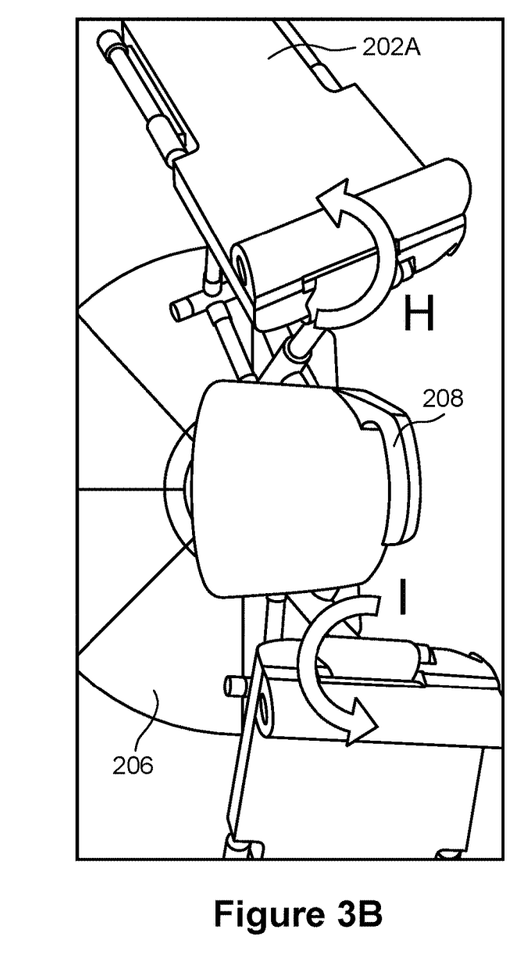

FIGS. 2A-2C illustrate various views of a patient positioning fixture (PPF) 200 that includes a rotating platform 206 on which the patient is positioned (e.g., in a seat 208). FIG. 2A illustrates an example view from the front of the PPF 200, where the armrests 202 and 204 are both in a "relaxed" position (e.g., position 202A and position 204A). FIG. 2B illustrates an example view from the top of the PPF 200 (e.g., from above). In FIG. 2B, both armrests are in the relaxed positions. FIG. 2C illustrates an example view from the front of the PPF 200 where the armrests exhibit "extreme armrest pitch" (e.g., where one armrest 204 is in the relaxed position (e.g., position 204A) and the other armrest 202 is articulated to the greatest extent (e.g., position 202B). In some embodiments, an extreme armrest pitch that is opposite from FIG. 2C is possible (e.g., armrest 204 is articulated to the greatest extent and the other armrest 202 is in the relaxed position).

The PPF 200 positions the patient in a seated position (e.g. a "3-legged stool" position"). In some embodiments, the seat is a conforming seat cushion. The seat 208 can be raised and lowered and pivots from front to back relative to the seated position. In some embodiments, the seat 208 cannot move from side-to-side as that would make the seat 208 highly unstable. In this position the patient is able to "sit" (rest) against a fixed position without affecting the standing breathing pattern. The seat 208 provides one leg of the stool and the patient provides the other two. Thus, the patient is in a 3-legged stool position during imaging. An x-ray detector panel is typically behind the patient.

The 3-legged-stool position provides a stable semi-standing resting position while the armrests 202 and 204, adjusted for patient height and shoulder width, provide the following benefits: (a) stabilizing the torso, (b) keeping the back straight in alignment with the rotational axis of the PPF, (c) keeping the arms in a non-stressed position and out of the x-ray imaging zone, and (d) keeping the patient in a comfortable, stable position without physical restraints. As can be noted, with the patient seated on the properly adjusted PPF, there is not much room laterally to move out of position, and with the armrests adjusted to the patient torso height, patient motion forward or backward is also constrained. In some embodiments, the PPF includes force measurement sensors on the arm rest to ensure that the armrest as snug against the patient.

The 3D optical sensing system 106 monitors patient position during x-ray imaging to determine patient location. In the event the patient moves outside of a pre-determined boundary, the x-ray imaging will pause and the computer system (e.g. computer system 406) will activate haptics in the applicable armrest to signal the patient to move toward the proper position. Once imaging begins, the absence of haptic outputs indicates that the patient is positioned properly. In some embodiments, the PPF 200 also includes haptics on the platform (e.g., that can be felt by the patient's feet). These haptics notify the patient that the platform is about to rotate.

As described in Application No. PCT/US2019/064846, the rotating platform rotates the patient with respect to an x-ray tube and detector panel. For example, instead of rotating the x-ray tube and detector panel, the PPF 200 rotates the patient between projection angles, acquires x-ray images at those projection angles, and keeps the patient's position substantially identical (e.g., fixed relative to the PPF 200) between rotations. In some embodiments, the x-ray images acquired at the different projection angles are used to model the dynamics of the patient's lung (e.g., how the lung moves during the breathing cycle). Identical patient position across projection angles is an aspect of image reconstruction and the radon transform: the object being reconstructed by its projections (e.g., the patient's lung) must be stationary (aside from movement from breathing) across all projection angles.

In some embodiments, as part of articulating the patient into a goal position, the following articulations are performed by the PPF 200, as illustrated in FIGS. 3A-3B. In some embodiments, shoulder motions performed by the PPF 200 include abduction (e.g., upward arm motion (A) of armrest 202 or 204 changing the angle of the arm), adduction (downward arm motion (F) of armrest 202 or 204 changing the angle of the arm), elevation (e.g., upward shoulder motion (E) of armrest 202 or 204 where the angle of the arm does not change), and depression (e.g., downward shoulder motion (C) of armrest 202 or 204 where the angle of the arm does not change). In some embodiments, elbow motions performed by the PPF 200 include flexion (e.g., upward arm curl (B)), extension (e.g., downward arm curl (G)), lateral rotation (e.g., outward rotation of armrest 202 or 204 away from the patient's body (H)), and medial rotation (e.g., rotation of component 202 or 204 towards the patient's body (I)). In some embodiments, knee motions performed by the PPF 200 include flexion (e.g., heel closer to body (D) where seat 208 is lowered towards the ground) and extension (e.g., heel away from body (D) where seat 208 is raised away from the ground).

As an example, in some embodiments, the PPF 200 patient positioning procedure is performed as follows (e.g., following the motions in FIGS. 3A-3B). In some embodiments, first, the seat 208 raises the patient into the x-ray's field of view (e.g., flexion knee movement D, where seat 208 is raised and/or lowered in relation to the ground). After raising the patient into the field of view of the x-ray, multiple operations can be performed to articulate the patient into the goal position 160. In some embodiments, the following motions are performed sequentially. In some embodiments, the following motions are performed concurrently. In some embodiments, the following motions can be performed in any order. In some embodiments, the following motions are performed partially sequentially and partially concurrently (e.g., at least two or more of the following motions are performed concurrently). In some embodiments, one or more of the following motions do not need to be performed to articulate the patient into the goal position 160.

In some embodiments, the armpit support(s) (e.g., armrest 202 and/or armrest 204) are raised and or lowered until tension is detected by the electromyographic sensors 108 connected to the patient (e.g., depression shoulder motion C and/or elevation shoulder motion E). In some embodiments, the arms are lifted away from the patient to move the arms outside the x-ray's field of view until tension is detected by the electromyographic sensors 108 (e.g., abduction arm motion A and/or adduction arm motion F). In some embodiments, the arms are rotated away from the torso to open a larger imaging projection arc until tension is detected by the electromyographic sensors 108 (e.g., outward rotation H and/or medial rotation I). In some embodiments, the elbows are laterally rotated for patient comfort and access to ECG leads, unless tension is detected by the electromyographic sensors 108 (e.g., upward arm curl B and/or downward arm curl G).

Figure 4:
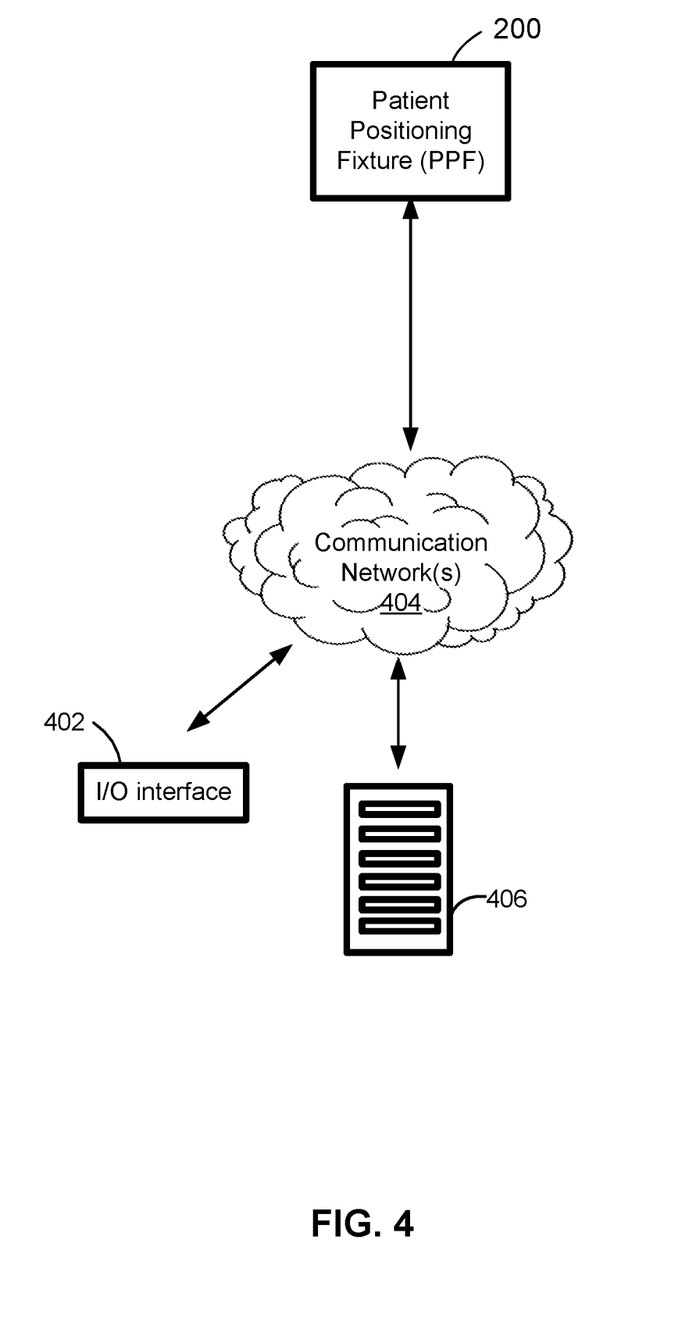
FIG. 4 illustrates example communications connections of various devices, in accordance with some embodiments of the present disclosure.

FIG. 4 illustrates example communication connections of various devices, in accordance with some embodiments of the present disclosure. For example, in some embodiments, PPF 200, computer system 406, and user interface 402 (e.g., an input/output device with a human-operable user interface, such as a desktop computer, laptop computer, tablet, mobile phone, or the like) communicate through one or more networks 404. In some embodiments, the one or more networks 404 include public communication networks, private communication networks, or a combination of both public and private communication networks. For example, the one or more networks 404 can be any network (or combination of networks) such as the Internet, other wide area networks (WAN), local area networks (LAN), virtual private networks (VPN), metropolitan area networks (MAN), peer-to-peer networks, and/or ad-hoc connections.

Figure 5:
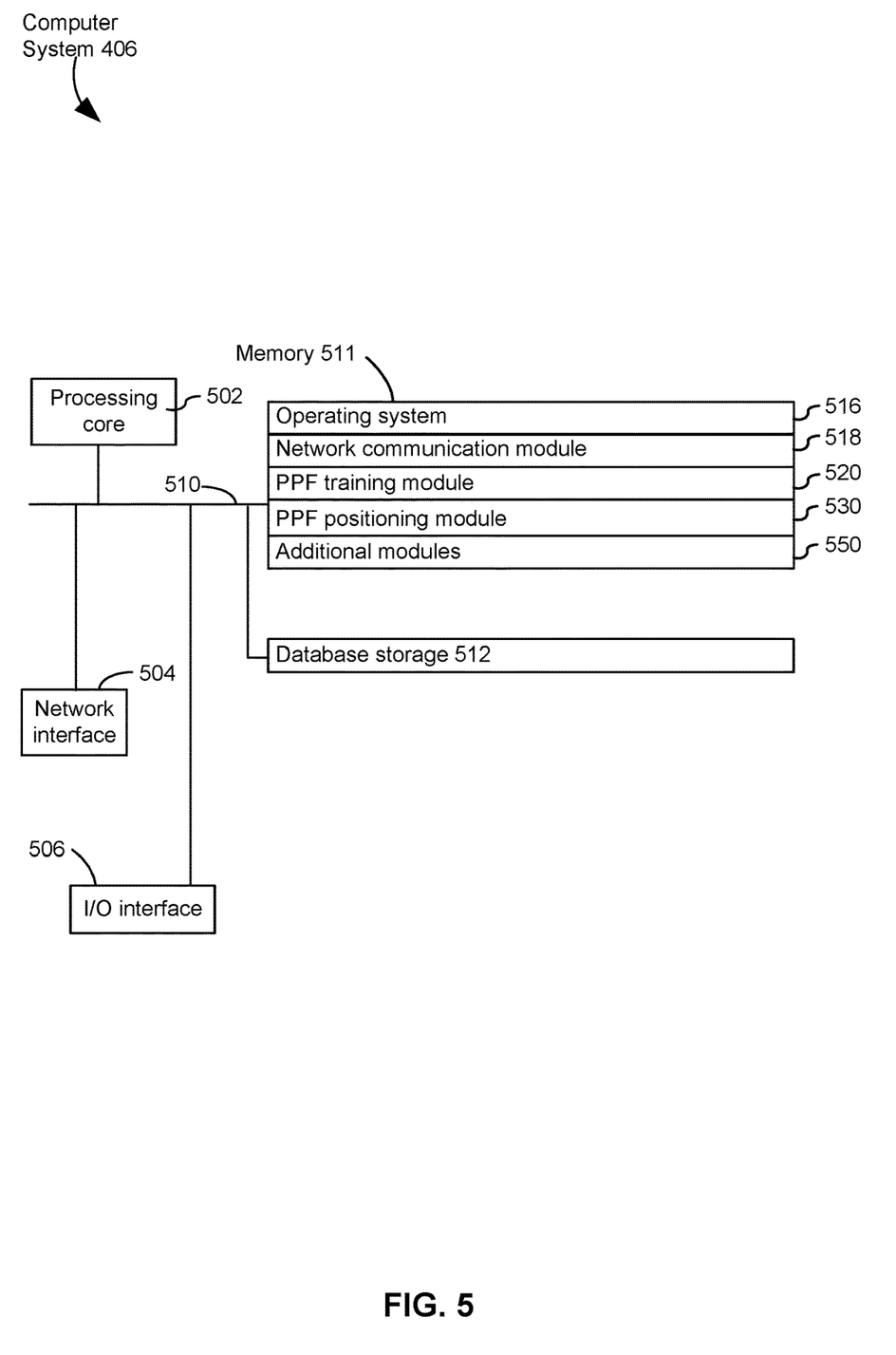
FIG. 5 illustrates a block diagram of a computer system (e.g., a computer control system), in accordance with some embodiments of the present disclosure.

Details of exemplary systems are now described in conjunction with FIG. 5. FIG. 5 illustrates an computer system 406 that contains instructions for training and/or moving a PPF 200 as described herein and as shown in FIGS. 2A-2C, 3A-3B, and 4. In some embodiments, computer system 406 includes one or more processing cores 502 (also referred to as processors), one or more network interfaces 504, memory 511 for storing programs and instructions for execution by the processing cores 502, one or more communications interfaces such as input/output (I/O) interface 506, and one or more communications buses 510 for interconnecting these components.

The one or more communication buses 510 optionally include circuitry (sometimes called a chipset) that interconnects and controls communications between system components. The memory 511 typically includes high-speed random access memory, such as DRAM, SRAM, DDR RAM, ROM, EEPROM, flash memory, CD-ROM, digital versatile disks (DVD) or other optical storage, magnetic cassettes, magnetic tape, magnetic disk storage or other magnetic storage devices, optical disk storage devices, flash memory devices, or other non-volatile solid state storage devices. Memory 511 optionally includes one or more storage devices remotely located from the processing cores 502 (e.g., CPU(s), ZISCs, and the like). Memory 511, and the non-volatile memory device(s) within the memory 511, comprise a non-transitory computer readable storage medium.

In some embodiments, the one or more processing cores 502 include a zero instruction set computer, which is used as described with reference to FIGS. 1A-1C.

In some embodiments, I/O interface 506 includes or is coupled with any of the sensors described with reference to FIG. 1A. In addition, in some embodiments, I/O interface 506 includes or is coupled with force sensors (e.g., in the armrest and/or seat). The force sensors in the armrest ensure that the armrest is snug against the patient, whereas the force sensors in the seat measure the patient's weight.

In some embodiments, memory 511 or alternatively the non-transitory computer readable storage medium stores the following programs, modules and data structures, or a subset thereof:
 Operating system 516, which includes procedures for handling various basic system services and for performing hardware dependent tasks;
 Network communication module (or instructions) 518 for connecting computer system 406 with other devices, or a communication network;
 PPF training module 520 for performing training 150 as described with regards to FIG. 1A, which includes:
 PPF positioning module 530 for performing automated positioning process 100 as described with regards to FIG. 1B, which includes:
 Optionally, other modules 550 that include instructions for handling other functions and aspects described herein.

In various implementations, one or more of the above identified elements are stored in one or more of the previously mentioned memory devices, and correspond to a set of instructions for performing a function described above. The above identified modules, data, or programs (e.g., sets of instructions) need not be implemented as separate software programs, procedures, datasets, or modules, and thus various subsets of these modules and data may be combined or otherwise re-arranged in various implementations. In some implementations, memory 511 optionally stores a subset of the modules and data structures identified above. Furthermore, in some embodiments, the memory stores additional modules and data structures not described above. In some embodiments, one or more of the above identified elements is stored in a computer system, other than that of computer system 406, that is addressable by computer system 406 so that computer system 406 may retrieve all or a portion of such data when needed.

Figure 6A:
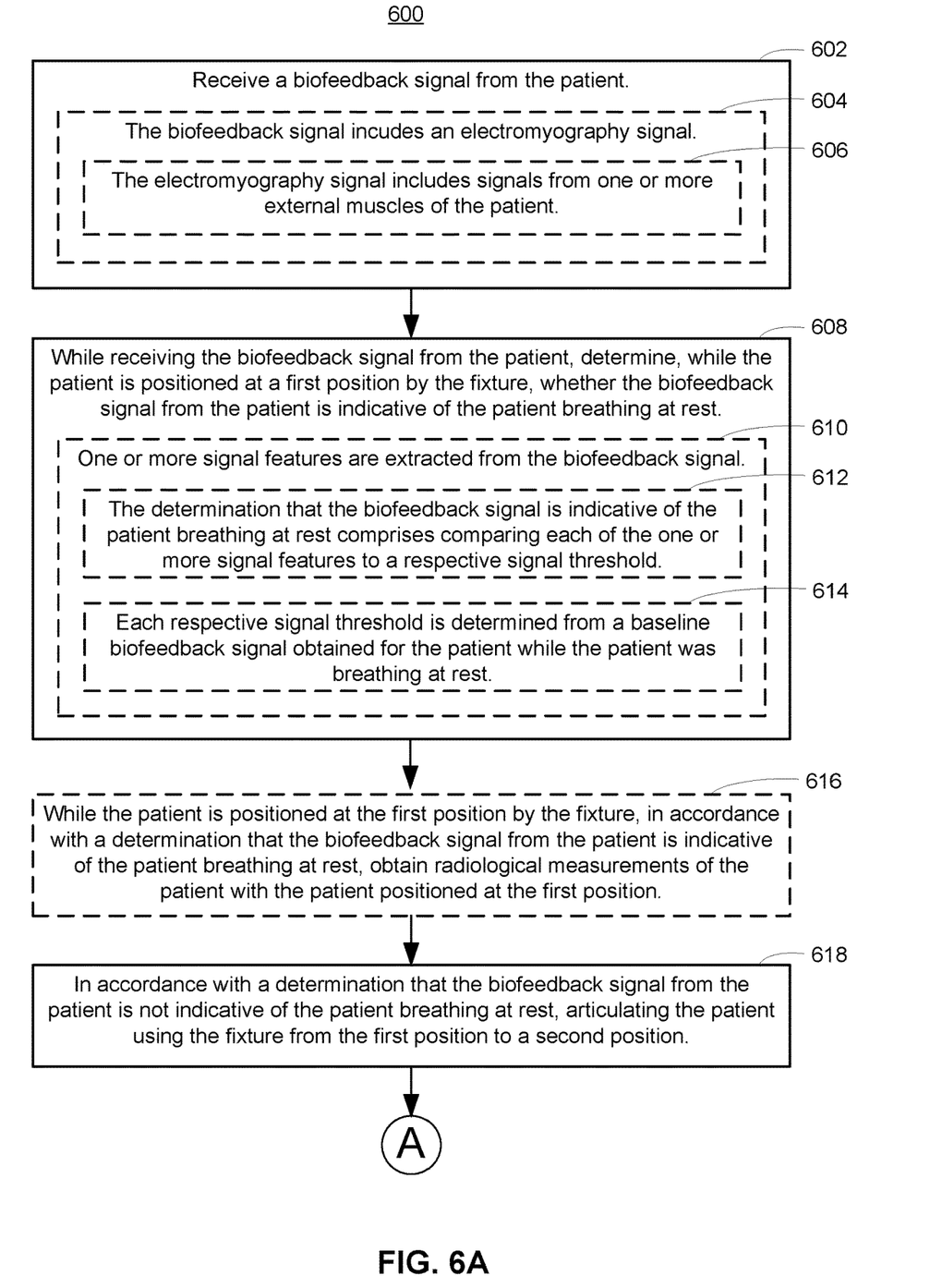
FIGS. 6A-6B illustrate a flowchart for a method of positioning a patient within a medical imaging (e.g., x-ray) apparatus, in accordance with some embodiments of the present disclosure.
Figure 6B:
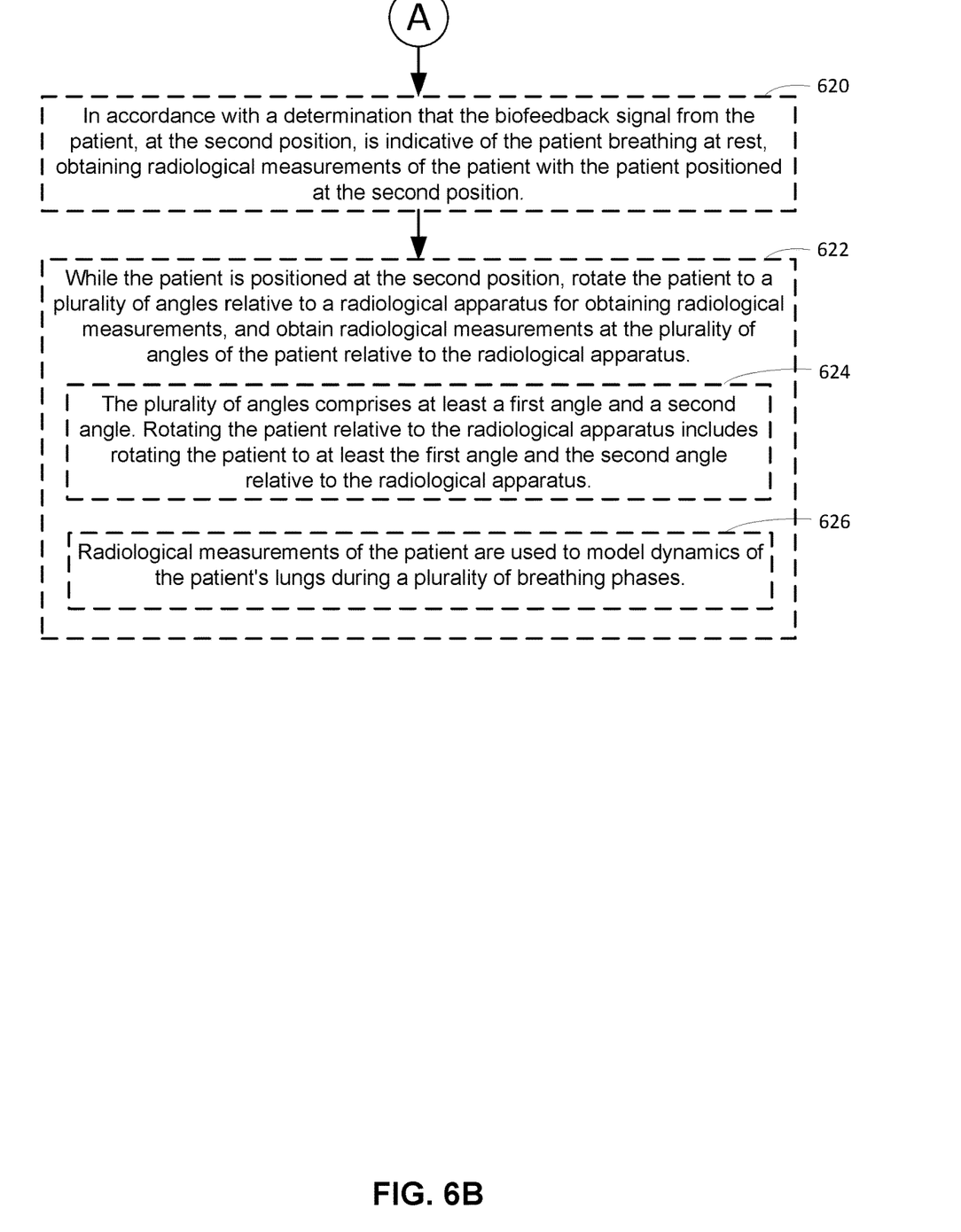

While systems and apparatuses in accordance with the present disclosure have been disclosed above, methods in accordance with the present disclosure are now detailed with regards to FIGS. 6A-6B.

FIGS. 6A-6B illustrate a flowchart for a method 600 of positioning a patient within a medical imaging (e.g., x-ray) apparatus, in accordance with some embodiments of the present disclosure. The method 600 is performed at a computer system with one or more processors, and memory (e.g., computer system 406, FIG. 4).

Block 602 of FIG. 6A. The method proceeds 602 by receiving a biofeedback signal from the patient. Referring to block 604, in some embodiments, the biofeedback signal includes an electromyography (EMG) signal. In some embodiments, the EMG signal is measured by the deltoid EMG sensor pair 108a, as shown in FIG. 1C and as described above. In some embodiments, the EMG signal is measured by the trapezius EMG sensor pair 108b, as shown in FIG. 1C and as described above. In some embodiments, the EMG signal is measured by the exterior oblique sensor pair 108c, as shown in FIG. 1C and as described above.

Referring to block 606, in some embodiments, the electromyography signal includes signals from one or more external muscles (e.g., oblique muscles) of the patient. In some embodiments, the electromyography signal is obtained using one or more electromyography sensors. In some embodiments, the electromyography signals include signals from the patient's external oblique muscle, trapezius muscle, and deltoid muscle.

Block 606 of FIG. 6A. The method proceeds 608 by, while receiving the biofeedback signal from the patient, determining, while the patient is positioned at a first position by the fixture, whether the biofeedback signal from the patient is indicative of the patient breathing at rest. In some embodiments, while the biofeedback signal is being received from the patient, the method makes a determination (e.g., a positive identification of the fact) that the biofeedback signal is, or is not, indicative of the patient breathing at rest.

Referring to block 610, in some embodiments, one or more signal features are extracted from the biofeedback signal.

Referring to block 612, in some embodiments, the determination that the biofeedback signal is, or is not, indicative of the patient breathing at rest comprises comparing each of the one or more signal features to a respective signal threshold.

Referring to block 614, in some embodiments, each respective signal threshold is determined from a baseline biofeedback signal obtained for the patient while the patient was breathing at rest (e.g., as determined from the training period as described above with regards to FIG. 1A).

Referring to block 616, in some embodiments, the method includes, while the patient is positioned at the first position by the fixture, in accordance with a determination that the biofeedback signal from the patient is indicative of the patient breathing at rest, obtaining radiological measurements of the patient with the patient positioned at the first position. In some embodiments, the radiological measurements are obtained based on a determination that the patient is at a goal position. In some embodiments, the radiological measurements are obtained based on a determination that the patient is as close as possible to a goal position (e.g., further articulation would result in the patient no longer breathing at rest).

In some embodiments, the method includes, prior to the patient being at the first position: determining, while the patient is positioned at a previous position by the fixture, whether the biofeedback signal from the patient is indicative of the patient breathing at rest. The method further includes, in accordance with a determination that the biofeedback signal from the patient is indicative of the patient breathing at rest, and that the first position is closer to a goal position than the previous position, articulating the patient using the fixture from the previous position to the first position. For example, when the patient is breathing at rest, but the patient is not yet at the goal position, the method includes attempting to articulate the patient further toward the goal position. In some embodiments, radiological measurements are obtained only when the patient is breathing at rest and the patient is either at the goal position or as close as possible to the goal position without altering the patient's breathing. To that end, in some embodiments, articulating the patient using the fixture from the previous position to the first position includes moving the patient's arms so as to provide a wider angle for radiological measurements of the patient's chest. Examples of such rotation movements include outward rotation H and/or medial rotation I, as described above with respect to FIGS. 3A-3B.

In some embodiments, while the biofeedback signal is being received from the patient (e.g., while the patient is positioned at the first position by the fixture), the method determines that the biofeedback signal is not indicative of the patient breathing at rest.

Block 618 of FIG. 6A. The method proceeds 618 by, in accordance with a determination that the biofeedback signal from the patient is not indicative of the patient breathing at rest, articulating the patient using the fixture from the first position to a second position. In some embodiments, the articulation in accordance with the determination that the patient is not breathing at rest is an articulation away from a goal position.

Block 600 of FIG. 6B. The method proceeds 620 by, in accordance with a determination that the biofeedback signal from the patient at the second position is indicative of the patient breathing at rest, obtaining radiological measurements of the patient with the patient positioned at the second position.

In some embodiments, the method proceeds by determining, while the patient is positioned at the second position by the fixture, whether the biofeedback signal from the patient is indicative of the patient breathing at rest. In some embodiments, in accordance with a determination that the biofeedback signal from the patient is not indicative of the patient breathing at rest, the method proceeds by articulating the patient (e.g., by using the fixture) from the second position to a third position. In some embodiments, in accordance with a determination that the biofeedback signal from the patient is indicative of the patient breathing at rest, the method proceeds by obtaining radiological measurements of the patient at the third position.

Block 622 of FIG. 6B. In any event, assuming that the patient is breathing at rest at the second position, the method proceeds 622 by, while the patient is positioned at the second position (e.g., in the frame of reference of the fixture), rotating the patient to a plurality of angles relative to a radiological apparatus (e.g., an x-ray system) for obtaining radiological measurements, and obtaining radiological measurements at the plurality of angles of the patient relative to the radiological apparatus. In some embodiments, the patient is rotated as a whole relative to the radiological apparatus. In some embodiments, a platform on which the patient is positioned (e.g., seated, standing, etc.) is rotated relative to the radiological apparatus. In some embodiments, prior to rotating the patient to the plurality of angles, a ramp rate (e.g., an angular acceleration) of the platform is determined based on a weight of the patient (e.g., as measured by force sensors in the seat). In some embodiments, the ramp rate is calculated so as to prevent inertial forces on the patient that would cause the patient to shift position in response to the rotation. In some embodiments, the patient is rotated to the plurality of angles using the ramp rate.

Referring to block 624, in some embodiments, the plurality of angles of the patient with regards to the radiological apparatus comprises at least a first angle and a second angle, and rotating the patient relative to the radiological apparatus includes rotating the patient to at least the first angle and the second angle relative to the radiological apparatus. In some embodiments, the first angle and the second angle are predetermined angles. In some embodiments, the first angle is a predetermined number of degrees (or radians) different than the second angle (e.g., the first and second angles will be 45 degrees apart). For example, if the predetermined number of degrees is 45 degrees and if the first angle is 10 degrees (e.g., the patient is initially rotated 10 degrees relative to the radiological apparatus), then the second angle will be 55 degrees.

In some embodiments, the re-positioning (e.g., articulating) of the patient (block 618) is mechanically constrained so as to assure that the axis of rotation (block 622) (e.g. the azimuthal angle) passes through an axis of a torso of the patient, as this assumption greatly simplifies the computer of the "3D image cubes" as described in PCT/US19/33751, filed May 23, 2019.

Block 626 of FIG. 6B. The method proceeds 626 by using radiological measurements of the patient to model dynamics of the patient's lungs during a plurality of breathing phases. In some embodiments, the plurality of breathing phases comprises all of the breathing phases in a breathing cycle (e.g., late inhalation (LI), mid-inhalation (MI), early inhalation (EI), late expiration (LE), mid-expiration (ME), and early expiration (EE) breathing phases). In some embodiments, the plurality of breathing phases comprises some of the breathing phases in a breathing cycle (e.g., at least 1, at least 2, at least 3, at least 4, at least 5, or at least 6 breathing phases). In some embodiments, the dynamics of the patient's lungs correspond to how the lungs move during the breathing cycle.

In some embodiments, the method includes, while the patient is at the second position and the patient is breathing at rest, determining that the position of the patient is not compliant. In some embodiments, the determination that the position of the patient is not compliant is made after obtaining a radiological measurement (e.g., during an acquisition phase of the method, as opposed to a training phase and/or positioning phase during which the patient's position is initially established). In some embodiments, the determination that the position of the patient is not compliant is made between radiological measurements. In some embodiments, the method includes delaying (or forgoing) a second radiological measurement in accordance with the determination that the position of the patient is not compliant.

In some embodiments, determining that the position of the patient is not compliant includes determining that the patient has deviated from the second position by more than a threshold amount (e.g., because the patient has shifted, slumped, or slouched). In some embodiments, the threshold amount is based on a tolerance for reconstructing a model of an organ of the patient. For example, when millimeter-level resolution of an internal organ (e.g., lung) of the patient is desired, the threshold amount is based on the tolerance needed for constructing the internal organ with millimeter-level resolution. In some embodiments, the threshold amount (based on the tolerance) is determined based on the radon transform.

In some embodiments, the determination that the position of the patient is not compliant is based on the biofeedback signal. In some embodiments, the determination that the position of the patient is non-compliant is based on a real-time 3D reconstruction of the patient (e.g., using LIDAR or another 3D imaging technology). In some embodiments, the real-time 3D reconstruction of the patient includes the internal model/rigging described with reference to FIGS. 1A-1C (e.g., LIDAR or another 3D imaging technology is used to determine various aspects of the shape of the patient, which is merged with an anatomical model of the patient to generate the 3D reconstruction, which is monitored and updated in real time).

In some embodiments, the method further includes, in accordance with the determination that the position of the patient is not compliant, providing a feedback signal to the patient (e.g., alerting the patient that their position (e.g., posture) is non-compliant). In some embodiments, the feedback signal is provided to the patient by one or more haptic devices (e.g. attached to the PPF). In some embodiments, the feedback signal includes a displayed representation of the patient's body (e.g., via a display that is viewable by the patient), and the displayed representation indicates how the patient should move to correct their position (e.g., posture).

Plural instances may be provided for components, operations, or structures described herein as a single instance. Finally, boundaries between various components, operations, and data stores are somewhat arbitrary, and particular operations are illustrated in the context of specific illustrative configurations. Other functional allocations are envisioned and may fall within the scope of the presently described implementation(s). In general, structures and functionality presented as separate components in the example configurations may be implemented as a combined structure or component. Similarly, structures and functionality presented as a single component may be implemented as separate components. These and other variations, modifications, additions, and improvements fall within the scope of the implementation(s).

It will also be understood that, although the terms first, second, etc. may be used herein to describe various elements and/or features, these elements and/or features should not be limited by these terms. These terms are only used to distinguish one element (and/or feature) from another. For example, a first widget could be termed a second widget, and, similarly, a second widget could be termed a first widget, without departing from the scope of the present disclosure. The first subject and the second subject are both widgets, but they are not the same widget.

The terminology used in the present disclosure is intended to describe particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises," "comprising," "including," "includes," "having," "has," "with," or variants thereof when used in this specification or claims, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting (the stated condition or event)" or "in response to detecting (the stated condition or event)," depending on the context.

The foregoing description included example systems, methods, techniques, instruction sequences, and computing machine program products that embody illustrative implementations. For purposes of explanation, numerous specific details were set forth in order to provide an understanding of various implementations of the inventive subject matter. It will be evident, however, to those skilled in the art that implementations of the inventive subject matter may be practiced without these specific details. In general, well-known instruction instances, protocols, structures, and techniques have not been shown in detail.

The foregoing description, for purpose of explanation, has been described with reference to specific implementations. However, the illustrative discussions above are not intended to be exhaustive or to limit the implementations to the precise forms disclosed. Many modifications and variations are possible in view of the above teachings. The implementations were chosen and described in order to best explain the principles and their practical applications, thereby enabling others skilled in the art to best utilize the implementations and various implementations with various modifications as are suited to the particular use contemplated.

What is claimed:

1. A method, comprising:
at a computer system with one or more processors and memory, wherein the computer system is communicatively coupled with a fixture for positioning a patient during radiological measurements, performing a set of operations, comprising:
receiving a biofeedback signal from the patient;
while receiving the biofeedback signal from the patient:
determining, while the patient is positioned at a first position by the fixture, whether the biofeedback signal from the patient is indicative of the patient breathing at rest; and
in accordance with a determination that the biofeedback signal from the patient is not indicative of the patient breathing at rest, articulating the patient using the fixture from the first position to a second position; and
in accordance with a determination that the biofeedback signal from the patient, at the second position, is indicative of the patient breathing at rest, obtaining radiological measurements of the patient with the patient positioned at the second position.

2. The method of claim 1, wherein the biofeedback signal incudes an electromyography signal.

3. The method of claim 2, wherein the electromyography signal includes signals from one or more external muscles of the patient.

4. The method of claim 1, further comprising:
while the patient is positioned at the first position by the fixture, in accordance with a determination that the biofeedback signal from the patient is indicative of the patient breathing at rest, obtaining radiological measurements of the patient with the patient positioned at the first position.

5. The method of claim 1, wherein one or more signal features are extracted from the biofeedback signal.

6. The method of claim 5, wherein the determination that the biofeedback signal is indicative of the patient breathing at rest comprises comparing each of the one or more signal features to a respective signal threshold.

7. The method of claim 5, wherein each respective signal threshold is determined from a baseline biofeedback signal obtained for the patient while the patient was breathing at rest.

8. The method of claim 1, further including:
prior to the patient being at the first position:
determining, while the patient is positioned at a third position by the fixture, whether the biofeedback signal from the patient is indicative of the patient breathing at rest; and
in accordance with a determination that the biofeedback signal from the patient is indicative of the patient breathing at rest, and that the first position is closer to a goal position than the third position, articulating the patient using the fixture from the third position to the first position.

9. The method of claim 8, wherein articulating the patient using the fixture from the third position to the first position includes moving the patient's arms so as to provide a wider angle for radiological measurements of the patient's chest.

10. The method of claim 1, further including:
while the patient is positioned at the second position:
rotating the patient to a plurality of angles relative to a radiological apparatus for obtaining radiological measurements; and
obtaining radiological measurements at the plurality of angles of the patient relative to the radiological apparatus.

11. The method of claim 10, wherein:
the plurality of angles comprises at least a first angle and a second angle; and
rotating the patient relative to the radiological apparatus includes rotating the patient to at least the first angle and the second angle relative to the radiological apparatus.

12. The method of claim 1, wherein while receiving the biofeedback signal from the patient:
determining, while the patient is positioned at the second position by the fixture, whether the biofeedback signal from the patient is indicative of the patient breathing at rest; and
in accordance with a determination that the biofeedback signal from the patient is not indicative of the patient breathing at rest, articulating the patient using the fixture from the second position to a third position.

13. The method of claim 1, wherein radiological measurements of the patient are used to model dynamics of the patient's lungs during a plurality of breathing phases.

14. The method of claim 1, further comprising:
while the patient is at the second position and the patient is breathing at rest:
determining that the position of the patient is not compliant; and
in accordance with the determination that the position of the patient is not compliant, providing a feedback signal to the patient.

15. The method of claim 14, wherein the feedback signal is provided by one or more haptic devices.

16. The method of claim 14, wherein the determination that the position of the patient is not compliant is based on the biofeedback signal.

17. A computer system communicatively coupled with a fixture for positioning a patient during radiological measurements, comprising:
one or more processors;
memory storing a set of instructions for:
receiving a biofeedback signal from a patient;
while receiving the biofeedback signal from the patient:
determining, while the patient is positioned at a first position by the fixture, whether the biofeedback signal from the patient is indicative of the patient breathing at rest; and
in accordance with a determination that the biofeedback signal from the patient is not indicative of the patient breathing at rest, articulating the patient using the fixture from the first position to a second position; and
in accordance with a determination that the biofeedback signal from the patient, at the second position, is indicative of the patient breathing at rest, obtaining radiological measurements of the patient with the patient positioned at the second position.

18. A non-transitory computer-readable storage medium storing instructions which, when executed by a computer system communicatively coupled with a fixture for positioning a patient during radiological measurements cause the computer system to perform a set of operations, comprising:
receiving a biofeedback signal from a patient;
while receiving the biofeedback signal from the patient:
determining, while the patient is positioned at a first position by the fixture, whether the biofeedback signal from the patient is indicative of the patient breathing at rest; and
in accordance with a determination that the biofeedback signal from the patient is not indicative of the patient breathing at rest, articulating the patient using the fixture from the first position to a second position; and
in accordance with a determination that the biofeedback signal from the patient, at the second position, is indicative of the patient breathing at rest, obtaining radiological measurements of the patient with the patient positioned at the second position.

* * * * *